United States Patent
Prescott et al.

(10) Patent No.: US 9,968,972 B2
(45) Date of Patent: May 15, 2018

(54) SURGICAL INSTRUMENT SANITIZER APPARATUS, SYSTEM, AND METHOD OF USE

(71) Applicant: Enteroptyx, Inc., Memphis, TN (US)

(72) Inventors: Anthony D. Prescott, Arlington, TN (US); Richard W. Mendius, Collierville, TN (US)

(73) Assignee: Enteroptyx, Inc., Memphis, TN (US)

( * ) Notice: Subject to any disclaimer, the term of this patent is extended or adjusted under 35 U.S.C. 154(b) by 712 days.

(21) Appl. No.: 14/476,689

(22) Filed: Sep. 3, 2014

(65) Prior Publication Data

US 2016/0059280 A1 Mar. 3, 2016

(51) Int. Cl.
| | |
|---|---|
| *A61L 2/18* | (2006.01) |
| *B08B 9/032* | (2006.01) |
| *B08B 3/10* | (2006.01) |
| *B08B 9/00* | (2006.01) |
| *A61B 90/70* | (2016.01) |
| *B08B 9/035* | (2006.01) |

(52) U.S. Cl.
CPC ............ *B08B 9/0321* (2013.01); *A61B 90/70* (2016.02); *A61L 2/18* (2013.01); *B08B 3/10* (2013.01); *B08B 9/00* (2013.01); *B08B 9/035* (2013.01)

(58) Field of Classification Search
CPC ......... B08B 9/0321; B08B 9/00; B08B 9/035; A61B 90/70
USPC ....................................................... 134/169
See application file for complete search history.

(56) References Cited

U.S. PATENT DOCUMENTS

| | | |
|---|---|---|
| 4,526,623 A | 7/1985 | Ishii et al. |
| 4,752,983 A | 6/1988 | Grieshaber et al. |
| 5,279,317 A | 1/1994 | Bowman et al. |
| 5,320,119 A | 6/1994 | Griffiths |
| 5,554,228 A | 9/1996 | Giordano et al. |
| 5,755,894 A | 5/1998 | Bowman et al. |
| 6,044,855 A | 4/2000 | Monch |
| 6,354,312 B1 | 3/2002 | Lin et al. |
| 6,948,505 B2 | 9/2005 | Karapetyan |
| 7,578,884 B1 | 8/2009 | Cetrangelo |
| 8,403,916 B2 | 3/2013 | Prescott |
| 8,741,069 B2 | 6/2014 | Meyer |

(Continued)

FOREIGN PATENT DOCUMENTS

EP 2314248 A1 4/2011

*Primary Examiner* — Michael E Barr
*Assistant Examiner* — Tinsae B Ayalew
(74) *Attorney, Agent, or Firm* — Gordon & Jacobson, P.C.

(57) ABSTRACT

A cleaning system includes a surgical tool assembly having a longitudinal shaft and a sleeve surrounding the longitudinal shaft. The system includes an injector head and body that receive the assembly. The head has an inlet coupling that fluidly couples to a pressurized fluid source. The body couples to the head to house the assembly between the head and the body. The body has an outlet coupling to fluidly couple to a vacuum source. When the assembly is housed between the head and the body, at least one fluid pathway is formed between the inlet coupling, the head, the shaft and the sleeve, the body, and the outlet coupling. A positive pressure fluid source is coupled to the inlet coupling and a vacuum source is connected to the outlet coupling to establish a pressure differential across the fluid pathway sufficient to draw the fluid therethrough.

18 Claims, 5 Drawing Sheets

(56) References Cited

U.S. PATENT DOCUMENTS

2013/0133698 A1   5/2013  Meyer
2014/0190523 A1*  7/2014  Garvey .................. A61B 90/70
                                                  134/22.12

* cited by examiner

SURGICAL INSTRUMENT SANITIZER APPARATUS, SYSTEM, AND METHOD OF USE

BACKGROUND

1. Field

The following relates to sanitizing surgical instruments, and more particularly to sanitizing surgical cutting tools. More specifically, the invention relates to a sanitizer for burs, such as those used during a stapedotomy and other surgical procedures. However, the sanitizing device disclosed herein can be easily adapted to use with other types of instruments such as orthopedic reamers and endoscopic shavers.

2. State of the Art

A high-speed cutting tool, such as a bur is used to drill into bone, such as the stapes or cochlea. After using the cutting tool, the tool can be cleaned for reuse or can be disposed. For reusable tools, due to tight tolerances within some cutting tool assemblies, debris and fluid from a surgical procedure may be located in hard to clean areas of the cutting tool assemblies rendering the tools difficult to clean for reuse. Such areas of the cutting tool, even if they can be reached for cleaning, may not be readily cleaned using systems available in a surgical theater within a reasonable amount of time.

SUMMARY

A surgical tool sanitizing system is provided for a surgical tool assembly having a longitudinal shaft and at least one bearing sleeve surrounding the longitudinal shaft. The system includes a sanitizing instrument constructed to house the surgical tool assembly. The sanitizing instrument has an injector head constructed to partially receive the surgical tool assembly. The injector head has an inlet coupling constructed to fluidly couple to a source of pressurized fluid. The sanitizing instrument also includes a sanitizing body constructed to at least partially receive and protect the tool assembly and constructed to connect to the injector head so that the tool assembly is housed between the injector head and the sanitizing body. The sanitizing body has an outlet coupling constructed to fluidly couple to a vacuum source. When the tool assembly is housed in the sanitizing instrument, at least one fluid pathway is formed between the inlet coupling, the injector head, the shaft and bearing sleeve of the tool assembly, the sanitizing body, and the outlet coupling. The system includes a fluid delivery device fluidly coupled to the inlet coupling. The fluid delivery device is constructed to deliver fluid at positive pressure to the injector head through the at least one fluid pathway to the outlet coupling. The system further includes a vacuum source fluidly coupled to the outlet coupling. The vacuum source is constructed to apply a negative pressure to the at least one fluid pathway. The positive pressure and the negative pressure establish a pressure differential sufficient to draw the fluid through the at least one fluid pathway of the tool assembly.

The injector head may be threadably or otherwise coupled to the sanitizing body such that at least a portion of the tool assembly is compressed between the injector head and the sanitizing body when they are coupled together. The injector head may be constructed to be threaded with respect to the sanitizing body into a seated configuration in which the injector head and the sanitizing body are sealed with each other around the tool assembly. In the seated configuration the tool assembly is completely contained in the sanitizing instrument and is seated between the injector head and the sanitizing body. In the seated configuration, the sanitizing instrument is sealed with the surgical tool assembly so that the fluid pathway extends at least across the entire length of the shaft of the tool assembly and the entire length between the shaft and the bearing sleeve. The injector head and the sanitizing body extend longitudinally and parallel to the tool assembly.

In use, the injector head can be uncoupled from the sanitizer body to load the tool assembly into the injector head for cleaning or to unload the tool assembly from the injector head after a cleaning operation is complete. Once the tool assembly is loaded and the injector head and sanitizing body are coupled together, the coupling of the injector head longitudinally translates the tool assembly into the bore of the sanitizing body until the tool assembly is seated and sealed between the injector head and the sanitizer body. With the tool assembly fully seated and sealed in the sanitizing instrument, pressurized fluid can be introduced to the injector head while negative pressure is applied at the sanitizing body so that a pressure differential is established to draw the fluid through at least one pathway between the injector head, through the tool assembly, and the sanitizing body. Where the tool assembly includes a longitudinal shaft, at least one bearing sleeve surrounding the longitudinal shaft, and a cutting tool, the at least one pathway includes at least a pathway over the entire length of the shaft and the entire length between the bearing sleeve and the shaft.

DETAILED DESCRIPTION

Figure 1:
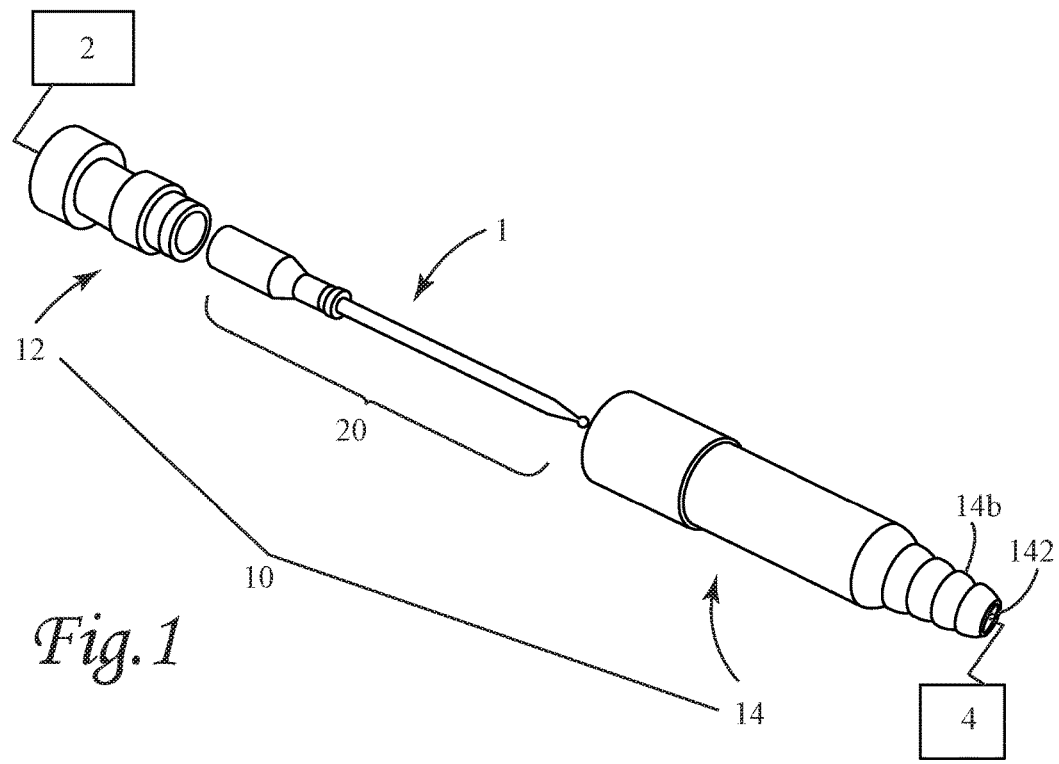
FIG. 1 is an isometric assembly view and part schematic view of an instrument sanitizing system, fluid delivery device, and vacuum source, in accordance with an aspect described herein.

Referring to FIG. 1, a sanitizing system 1 according to an embodiment of the invention is shown along with a fluid delivery device 2 and vacuum source 4. The system 1 includes a surgical instrument sanitizer 10 for a replaceable tool assembly 20. The instrument sanitizer 10 includes an injector head 12 and a sanitizing body 14. The replaceable tool assembly 20 is constructed to be secured and sanitized inside the instrument sanitizer 10, as described in greater detail below.

Figure 7:
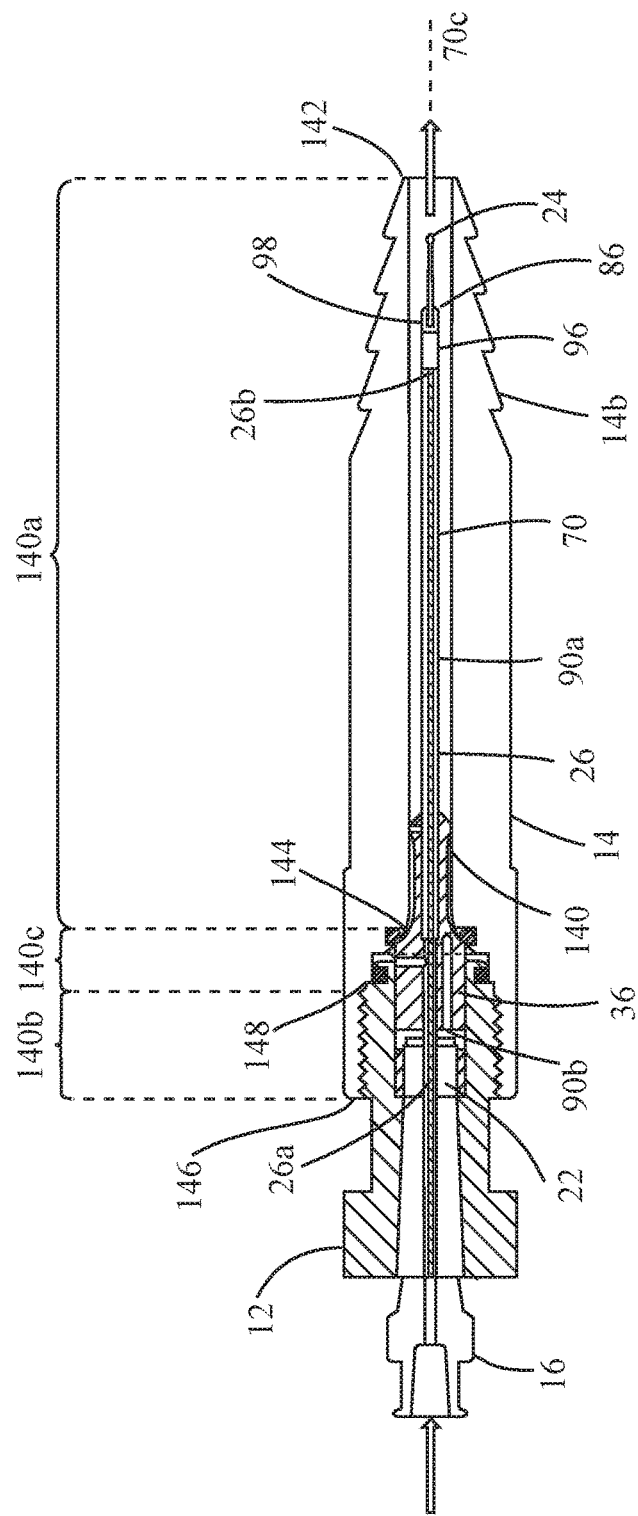
FIG. 7 is sectional view of the system shown in FIG. 5, viewed along section 7-7 in FIG. 5.
Figure 8:
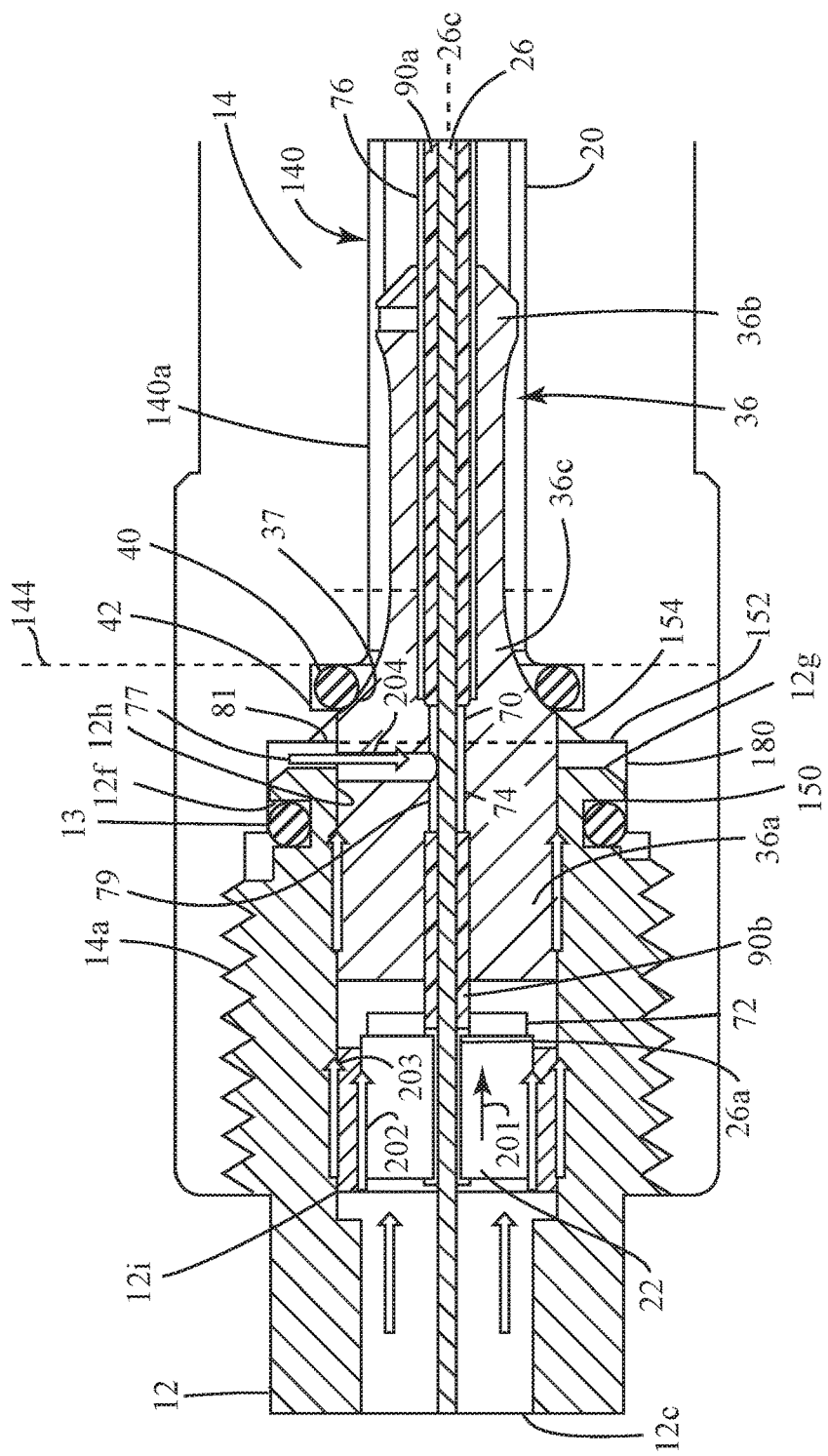
FIG. 8 is a partial exploded section view of the part noted in FIG. 7.

Referring momentarily to FIGS. 7 and 8, the replaceable tool assembly 20 includes a tool holder body 36, a tool shaft 26, a cutting tool in the form of a bur bit 24 (FIG. 7), and bearing sleeves 90a and 90b, all described in more detail below. For purposes of an exemplary surgical procedure where the cutting tool might be used, i.e., performing a cochleostomy, the cutting bur 24 preferably has a diameter of less than 1 mm.

As shown most clearly in FIG. 8, the tool holder body 36 of the tool assembly 20 has a proximal portion 36a, a distal portion 36b, and a tapered neck portion 36c between the proximal portion 36a and distal portion 36b. A longitudinal bore 70 extends longitudinally through the entire tool holder body 36. The tapered neck portion 36c provides a surface 37 that is suitable to seal against an o-ring seal 40 that is disposed in an annular groove 42 formed in the sanitizing body 14. The longitudinal bore 70 has an enlarged proximal portion 72, a relatively narrower central portion 74, and an enlarged distal portion 76, which may be threaded. Also, a side bore 77 is formed in the distal portion 36b of the tool holder body 36. The side bore 77 extends from an outer surface 81 of the proximal portion 36a of the tool holder body 36 into fluid communication with the longitudinal bore 70. The side bore 77 may extend transversely to the longitudinal bore 70 or may extend at another angle with the longitudinal bore. The side bore 77 is located at a distal end of the proximal portion of the holder body.

Bearing sleeves 90a and 90b extend longitudinally within the bore 70 and are longitudinally and preferably rotationally fixed relative to the bore 70, e.g., sleeve 90a is fixed by interference engagement at a notch 96 at a distal end of the bearing sleeve 90a. The rotatable tool shaft 26 extends from a proximal end 26a to a distal end 26b through the bearing sleeves 90a and 90b. Bearing sleeves 90a and 90b are longitudinally spaced from each other across a narrow central portion 74, such that an annular space 79 is formed between the shaft 26 and the bore narrow central portion 74 of the bore 70. The space 79 permits, among other things, fluid from the side bore 77 to flow into the space 79, as shown in FIG. 8, and move between shaft 26 and bearing sleeve 90a, as discussed in greater detail below.

Referring to FIG. 7, the distal end 26b of the tool shaft 26 carries a bur holder 98 that receives the bur bit 24. The bur holder 98 may be permanently integrated with the bur bit 24 or may be adapted to permit an exchange of one bit for another, i.e., selective release and secure capture of a bit. The tool shaft 26 is securely supported by, but rotatable within, the bearing sleeves 90a and 90b about a tool shaft axis 26c (FIG. 8) coaxial with a bore axis 70c of the bore 70, and is preferably made from spring steel wire or tubing with an outer diameter in the range of 0.020 to 0.028 inches.

The diameter of the bearing sleeves 90a and 90b are preferably small enough to contact the tool shaft 26 to prevent wobbling or lateral movement of the tool shaft 26, but not so small as to restrict rotation or longitudinal translation of the tool shaft 26 relative to the bearing sleeves 90a and 90b. In one embodiment, the inner diameter of the bearing sleeves 90a and 90b are nominally 0.030 inch, such that the clearance between the tool shaft 26 and the bearing sleeves 90a and 90b is between 0.002 to 0.01 inch. The clearance between the tool shaft 26 and the bearing sleeves 90a and 90b, although relatively small, allows space for debris to accumulate during a cutting operation using the bur bit 24. Such debris must be removed and the surfaces of the tool assembly must be cleaned and sanitized in order for the tool assembly 20 to be reused.

The proximal end 26a of the tool shaft 26 is coupled to drive means 22 for driving the shaft 26. In a preferred embodiment, the drive means 22 include one or more drive magnets for a magnetic drive system of a drill handpiece (not shown), or appropriate means for engagement with a pneumatic drive system, hydraulic drive system or a direct or reduction-gear electric drive system to provide for controlled high speed rotation of the tool shaft 26 and consequently a bur bit 24. For example, a magnetic drive system with drive magnets 22 is described in more detail in U.S. Pat. No. 8,403,916.

After the tool assembly 20 is used in a surgical procedure it may be reusable for another procedure after any fluid and particulate debris accumulated in the tool assembly is removed and the tool assembly is cleaned and sanitized. However, as noted above, in at least one embodiment, the internal clearances of the tool assembly 20 are relatively small, especially between the shaft 26 and the bearing sleeve 90, which can cause a restriction to fluid flow therebetween. The use of the sanitizing instrument 10 with the tool assembly 20 facilitates a flow of fluid, such as cleaning fluid and/or water, through the internal clearance spaces of the tool assembly 20 to remove debris and clean and sanitize the tool assembly 20, as described in greater detail hereinbelow.

Figure 2:
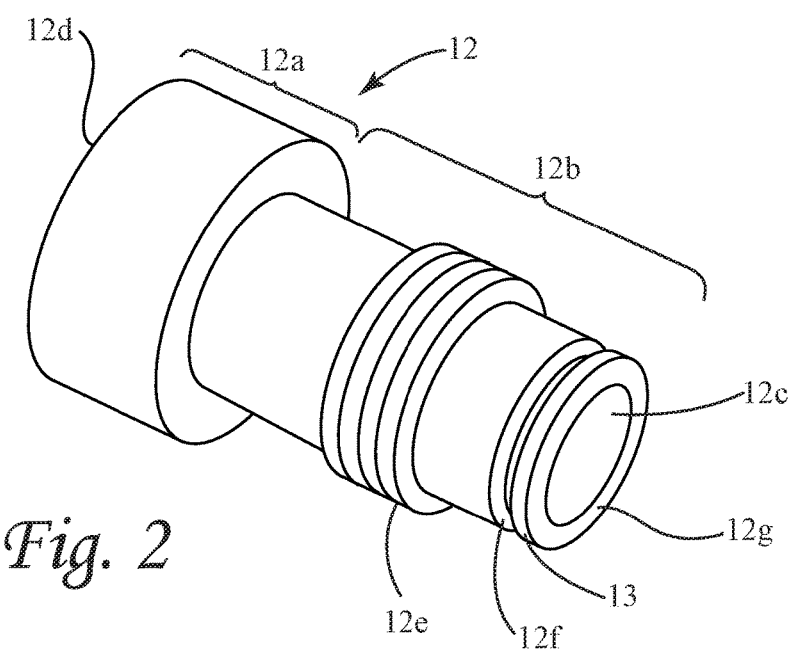
FIG. 2 is an isometric view of an injector head shown in FIG. 1.
Figure 6:
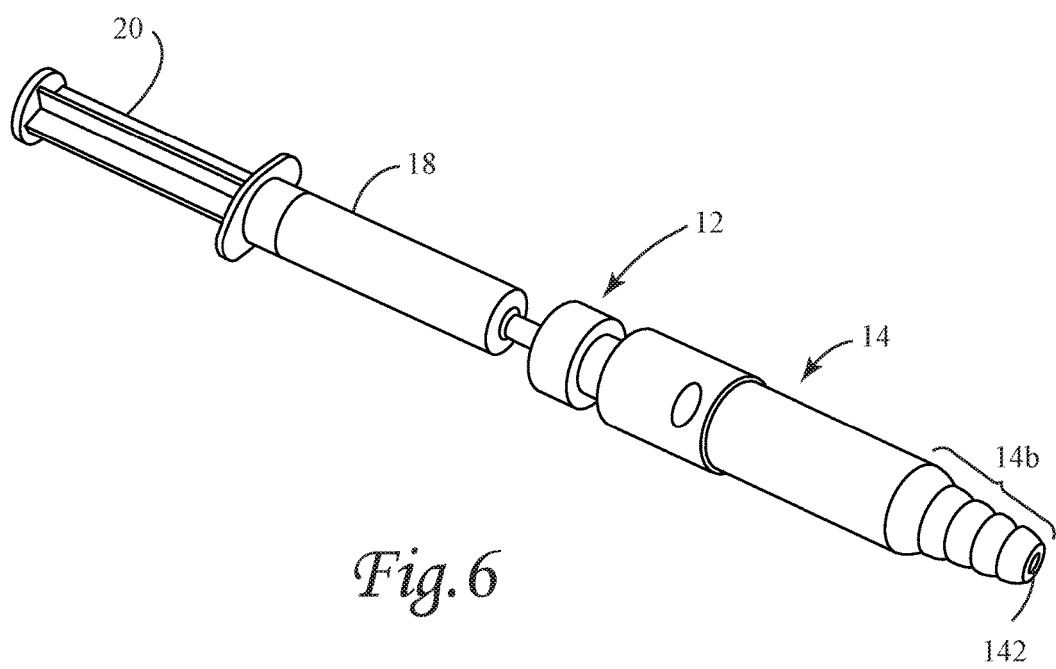
FIG. 6 is a view of the assembled system shown in FIG. 5 fluidly coupled to a syringe.

The injector head 12 of the sanitizing instrument 10 is shown in greater detail in FIG. 2. The injector head 12 has a proximal portion 12a and a distal portion 12b and a longitudinal bore 12c extending through the injector head 12. A connector 16 (FIG. 4), such as a luer lock, is provided at a proximal end 12d of the injector head 12, for connecting to a fluid delivery device 2 (FIG. 1), such as a syringe 18 (FIG. 6). The connector 16 is in fluid communication with the bore 12c.

The distal portion 12b of the injector head 12 is stepped with respect to the proximal portion 12a, which has a relatively smaller outer diameter. Male threads 12e extend around a portion of the distal portion 12b. The external male threads 12e are constructed to engage with internal female threads 14a (FIGS. 4 and 8) of the sanitizer body 14. Other connections between the distal portion 12b and sanitizer body 14 are possible, including, for example, a bayonet locking structure. Also, an o-ring seal 13 (FIGS. 2 and 8) is disposed in an annular groove 12f (FIGS. 2 and 8) formed on the distal portion 12b at a location between the threads 12e and a distal end 12g of the injector head 12. The outer surface of the proximal portion 12a is constructed to be grasped for rotation so that the injector head 12 can be threaded into or out of engagement with the sanitizer body 14. The o-ring 13 is constructed to seal with the sanitizer body 14 when the threads 12e of the injector head 12 and the threads 14a of the sanitizer body 14 are fully engaged, as shown in FIGS. 7 and 8.

Figure 3:
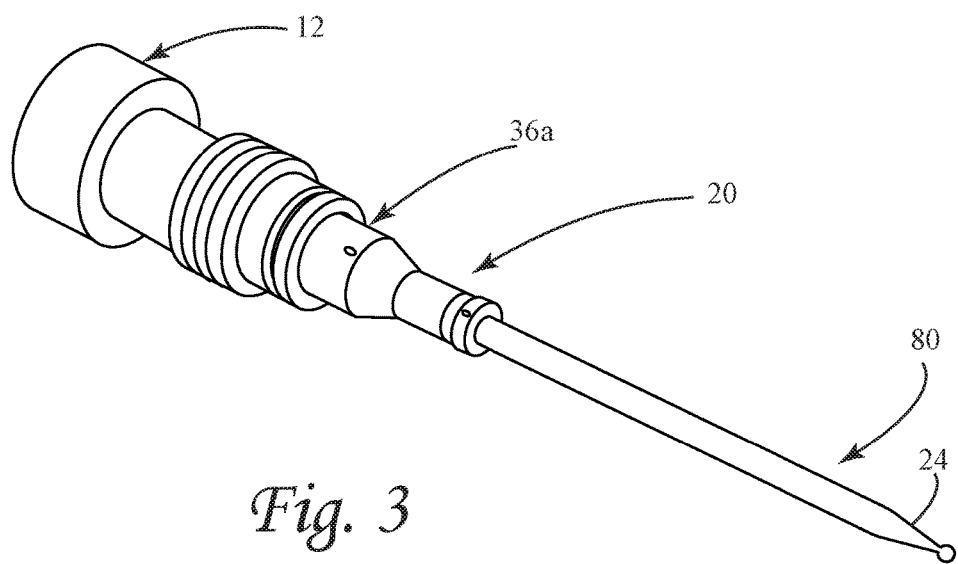
FIG. 3 is an isometric view of the injector head shown in FIG. 2 assembled with a tool assembly shown in FIG. 1.

The bore 12c is constructed to at least partially receive the tool holder body 36. For example, FIG. 3 shows at least a portion of the proximal portion 36a of the tool holder body 36 received in the bore 12c of the injector head 12. As shown most clearly in FIG. 8, the bore 12c has a receiving portion 12h that extends proximally from the distal end 12g of the injector head 12 to an annular ridge 12i. The ridge 12i acts as a longitudinal stop and a seat that contacts the proximal end of the tool holder body 36. The diameter of the receiving portion 12h is slightly larger than the outer diameter of the proximal portion 36a of the tool holder body 36 to provide an annular space therebetween that permits fluid flow in the annular space when the tool holder body 36 is seated in the receiving portion 12h and the tool assembly 20 is positioned in the instrument 10 for cleaning, as shown in FIGS. 7 and 8. The bore 12c of the injector head is coaxial with the longitudinal bore 70 of the tool holder body 36 so that they form a longitudinal pathway through the injector head 12 and tool holder body 36, as described in greater detail below.

Figure 4:
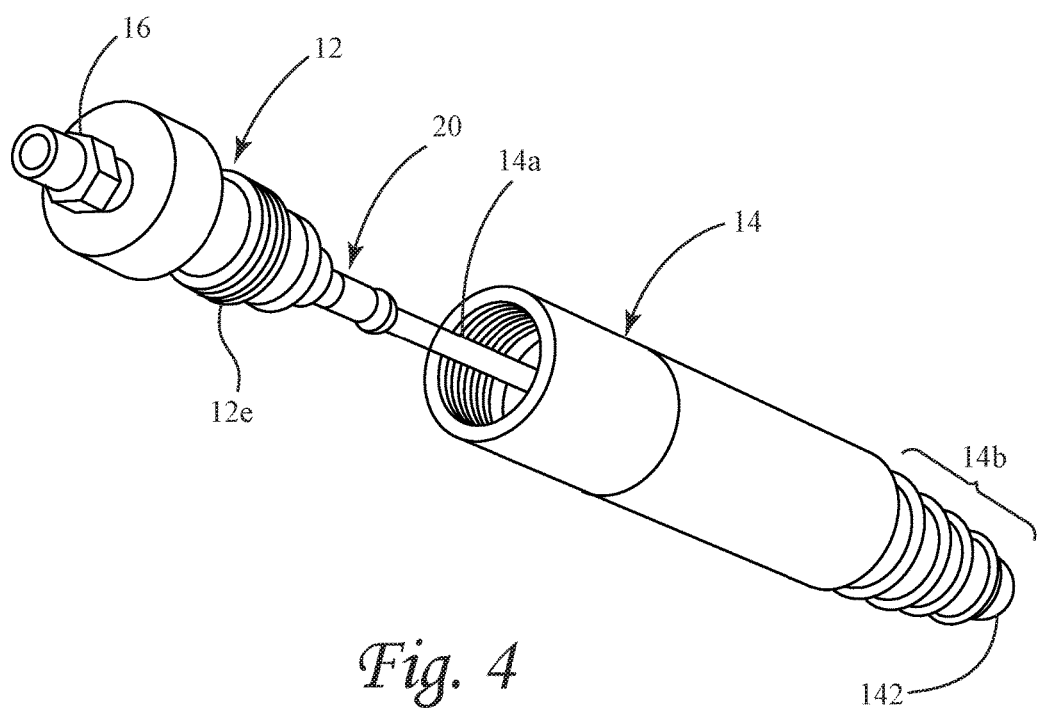
FIG. 4 is an isometric view of the system shown in FIG. 1, partially assembled.
Figure 5:
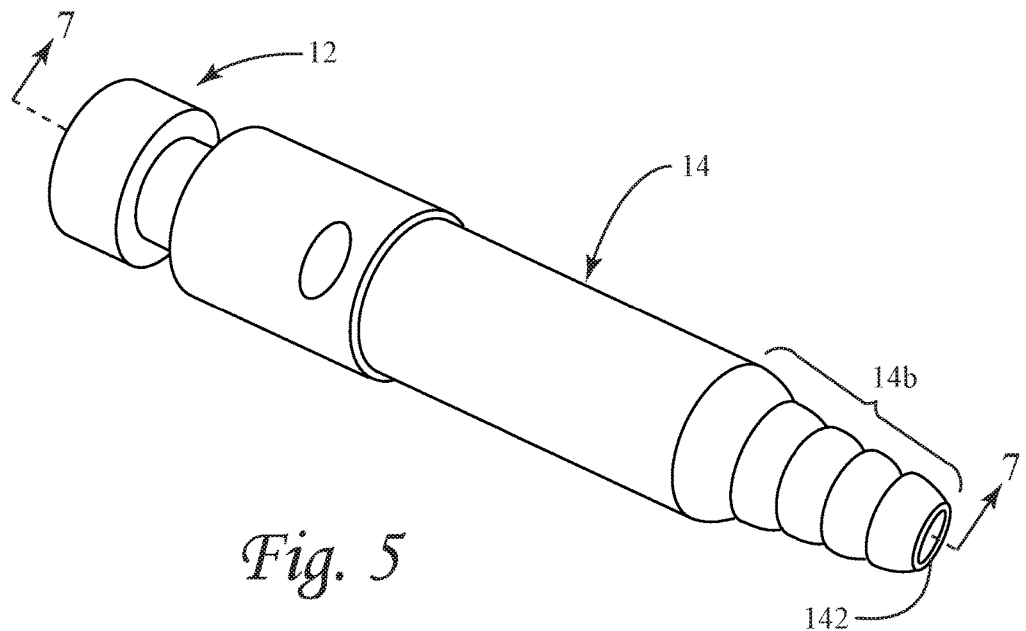
FIG. 5 is an isometric view of the system shown in FIG. 1, fully assembled.

The injector head 12 and the tool assembly 20 together can be inserted into sanitizing body 14, as shown in FIG. 4.

As shown in FIG. 7, the sanitizing body 14 has a longitudinal bore 140 that is constructed to receive the tool assembly 20 and the injector head 12. The bore 140 has a distal portion 140a that extends proximally from an open distal end 142 of the sanitizing body 14 to a proximal end 144 of the distal portion 140a. The distal portion 140a has a diameter that is slightly larger than the diameter of the distal portion 36b of the tool holder body 36.

The bore 140 also has a proximal portion 140b that extends distally from a proximal end 146 of the sanitizing body 14 to a distal end 148. The proximal portion 140b has internal threads 14a constructed to thread with external threads 12e of the injector head 12.

Also, the bore 140 also has a central portion 140c that extends between the distal portion 140a and the proximal portion 140b. As best shown in FIG. 8, the central portion 140c is defined by an annular wall 150 extending distally from the distal end 148 of the proximal portion 140b to an annular seat 152. The central portion 140c also is defined by a tapered section 154 that tapers distally from an inner diameter of the annular seat 152 to the annular groove 42 that extends to the proximal end of the distal portion 140a of the bore 140. The diameter of the annular wall 150 is shown as being larger than the diameter of the annular groove 42. The afore-mentioned o-ring seal 40 is disposed in the groove 42 and is configured to seal with the tapered neck 36c of the tool holder body 36, as shown in FIG. 8.

As shown in FIGS. 1 and 4 to 7, the sanitizing body 14 has a tapered barb 14b at distal end 142. The barb 14b is constructed to fit into a tube (not shown) of a vacuum source 4 (FIG. 1). Of course, it will be appreciated by those of ordinary skill in the art, that the sanitizing body 14 can be constructed with alternative connections instead of barb 14b. For example, the sanitizing body 14 can be constructed with a luer lock fitting at the distal end 142 to connect to a mating connector of the vacuum source.

In use, the injector head 12 can be unscrewed from the sanitizer body 14 to load the tool assembly 20 into the injector head 12 for cleaning or to unload the tool assembly 20 from the injector head 12 after a cleaning operation is complete. To load the tool assembly 20 into the injector head 12, the proximal portion 36a of the tool holder 36 is inserted into the bore 12c of the injector head 12, as shown in FIG. 3. With the proximal portion 36a of the tool holder body 36 inserted into the injector head 12, the remainder of the tool assembly 20 can be guided into the sanitizer body 14, as shown in FIG. 4. Once the external threads 12e engage the internal threads 14a, the injector head 12 is threaded to the sanitizing body 14 to longitudinally translate the tool assembly 20 into the bore 140 of the sanitizing body 14 until at least seal 13 seals with annular wall 150 and seal 40 seals with tapered neck 36c, in which case the tool assembly is considered fully seated in the sanitizing instrument 10, as shown in FIGS. 7 and 8, for example.

With the tool assembly 20 fully seated in the sanitizing instrument 10, fluid pathways denoted by arrows 201, 202, 203, and 204 in FIG. 8 are defined between injector head 12, tool assembly 20, and sanitizing body 14 so that a pressurized fluid introduced in the injector head 12 can flow through the tool assembly 20 and out the sanitizing body 14 during a cleaning operation, described in greater detail below.

The connector 16 can be fluidly coupled to the syringe 18 as shown in FIG. 6 and the barb 14 can be fluidly coupled to the vacuum source 4. The syringe 18 is preloaded with a fluid (e.g., cleaning fluid and/or water). To clean the tool assembly 20, fluid from the syringe 18 is introduced at a positive pressure into the injector head 12 by pushing on plunger 20 while a negative pressure is applied simultaneously to the sanitizer body 14 by the vacuum source 4. Negative and positive pressure refer, respectively, to relative pressures below and above atmospheric pressure. The positive and negative pressures provided by the syringe and the vacuum source establish a pressure differential sufficient to draw the fluid through the fluid pathways. The fluid drawn through the fluid pathways displaces debris and cleans and sanitizes the surfaces that define the pathways.

In at least one example, the syringe and the vacuum source establish a 31 psi differential pressure, which is sufficient to draw the fluid through the fluid pathways. In such an example, about 6 psi of differential vacuum is needed to be provided by the vacuum source 4, while about 25 psi of positive pressure is needed to be provided by the syringe. The foregoing examples are calculated as follows. A typical 6 ml syringe has a ½" diameter plunger, having a cross sectional area of 0.2 square inch. According to NASA a human male can apply 7 lbf with their thumb for extended periods of time. Assuming only 70% of the 7 lbf is applied, the pressure generated on the fluid in the 6 ml syringe would be about 25 psi (5 lbf/0.2 square inch=25 psi). In testing it has been shown that the combined use of positive and negative pressures to establish a pressure differential can speed up the cleaning of the tool assembly 20 when compared to applying only positive or negative pressures alone. Moreover, increasing the pressure differential, say be applying a relatively larger positive pressure with the syringe 18 can further reduce the cleaning time. For example, hospital gasses are generally pressurized at about 50 to 59 psig. Thus, if one were to use a syringe pressurized using such hospital gasses, the total differential could be about 65 psig (59 psig−(−6) psig=65 psig).

Upon introduction of fluid with a sufficient pressure differential established by the combination of the syringe 18 and vacuum source 4, the fluid moves through the bore 12c of injector head into and around the proximal portion 36a of the tool holder body 36, as shown by the arrows shown in FIG. 8. Some of the fluid from the syringe 18 enters the tool holder body 36 through a space between the bore 70 and tool shaft 26 as indicated by arrow 201. Some of the fluid from the syringe 18 enters the tool holder body 36 between an annular space between the magnet 22 and the tool holder body 36, as indicated by arrow 202. Also, some of the fluid from the syringe 18 moves around the proximal portion 36a of the tool holder body 36 between the receiving portion 12h of the bore 12c of the injector head 12 and the tool holder body 36, as indicated by arrow 203. The flows indicated by arrows 202 and 203 move in the annular space between the proximal portion 36a and the receiving portion 12h to a space 180 defined between the proximal end 12g of the injector head 12 and annular wall 150, annular seat 152, and tapered portion 154 of the sanitizing body 14. The fluid received in space 180 is redirected by its defining surfaces into the side bore 77 as indicated by arrow 204 and flows into space 79. The fluid flow denoted by arrow 201 can pass between the relatively small clearance between the bearing sleeve 90b and shaft 26 so that it also passes into space 79. The fluid flowing into space 79 then flows distally between shaft 26 and bearing sleeve 90a all the way to the bur bit 24. The fluid washes over the bur bit 24 to clean the bit, upon which the fluid is discharged out of the distal end 142 of the sanitizing body 14. Thus, all of the fluid introduced by the syringe 18 cleans the entire surface of the shaft 26, the bit 24, and the inner surfaces of the bearing sleeves 90a and 90b. When sufficient amount of fluid passes through the instrument (or a sufficient time of fluid flow has elapsed), fluid flow is stopped and the sanitizing instrument 10 can be opened by unscrewing the injector head 12 from the sanitizing body 14 to remove the cleaned tool assembly 20 therefrom.

There have been described and illustrated herein embodiments of a sanitizing system, sanitizing instrument, and a method of cleaning a tool assembly. While particular embodiments of the invention have been described, it is not intended that the invention be limited thereto, as it is intended that the invention be as broad in scope as the art will allow and that the specification be read likewise. Thus, while a particular injector head, tool assembly, and sanitizing body configuration has been disclosed, it will be appreciated that another conforming arrangement can be used as well, provided that such arrangement allows for fluid to clean the entire facing surfaces of the shaft and bearing sleeves of the tool assembly while the tool assembly is housed between the injector head and the sanitizing body. Also, while a bur has been shown as an exemplary cutting tool, other cutting tools can similarly be provided to the distal end of the shaft, including, for example, hollow cutting tools and arthroscopic shaver blades and orthopedic intramedullary reamers. It will therefore be appreciated by those skilled in the art that yet other modifications could be made to the provided invention without deviating from its spirit and scope as claimed.

What is claimed is:

1. A sanitizing instrument for cleaning a surgical tool or tool assembly having a longitudinal shaft, at least a sleeve surrounding the longitudinal shaft, and a cutting tool connected to the shaft, comprising:
    a source of pressurized fluid constructed to deliver fluid at a positive pressure;
    a vacuum source constructed to apply a negative pressure;
    an injector head constructed to at least partially receive the surgical tool assembly, the injector head having an inlet coupling constructed to fluidly couple to the source of pressurized fluid;
    a sanitizing body constructed to at least partially receive the tool assembly and constructed to connect to the injector head so that the tool assembly is housed between the injector head and the sanitizing body, the sanitizing body having an outlet coupling constructed to fluidly couple to the vacuum source,
    wherein when the tool assembly is housed in the sanitizing instrument at least one fluid pathway is formed between the inlet coupling, the injector head, between the shaft and the sleeve of the tool assembly, the sanitizing body, and the outlet coupling, and
    wherein the source of pressurized fluid and the vacuum source are configured to simultaneously apply positive and negative pressure while the fluid is introduced to establish at least a predetermined pressure differential sufficient to draw the fluid through the at least one fluid pathway.

2. The sanitizing instrument according to claim 1, wherein the injector head is threadably connected to the sanitizing body such that at least a portion of the tool assembly is compressed between the injector head and the sanitizing body when they are threaded together.

3. The sanitizing instrument according to claim 2, wherein the injector head is constructed to be threaded with respect to the sanitizing body into a seated configuration in which the injector head and the sanitizing body are sealed with each other around the tool assembly.

4. The sanitizing instrument according to claim 3, wherein in the seated configuration the tool assembly is completely contained in the sanitizing instrument and is seated between the injector head and the sanitizing body.

5. The sanitizing instrument according to claim 4, wherein in the seated configuration, the sanitizing instrument is sealed with the surgical tool assembly so that the fluid pathway extends at least across the entire length of the shaft of the tool assembly and the entire length between the shaft and the sleeve.

6. The sanitizing instrument according to claim 5, wherein the injector head and the sanitizing body extend longitudinally parallel to the tool assembly.

7. The sanitizing instrument according to claim 1, further comprising a seal retained in the injector head and a seal retained in the sanitizing body.

8. The sanitizing instrument according to claim 7, wherein the seals are spaced longitudinally from one another.

9. The sanitizing instrument according to claim 8, wherein the seals are spaced around a side bore of the tool assembly when the tool assembly is seated within the sanitizing instrument.

10. The sanitizing instrument according to claim 1, wherein a longitudinal axis of the inlet coupling is configured to extend parallel with respective longitudinal axes of the sanitizing body and the longitudinal shaft of the surgical tool.

11. The sanitizing instrument according to claim 10, wherein the surgical tool extends along a longitudinal axis from a proximal end configured to be received in the injector head to a distal end at the cutting tool, and wherein when the surgical tool is housed between the injector head and the sanitizing body, the inlet coupling of the injector head is located proximally of the proximal end of the surgical tool and the outlet coupling of the sanitizing body is located distally of the distal end of the surgical tool.

12. The sanitizing instrument according to claim 11, wherein the at least one fluid pathway causes fluid to flow from the inlet coupling to the outlet coupling around and through the surgical tool housed in the instrument.

13. A surgical tool sanitizing system, comprising:
    a surgical tool assembly having a longitudinal shaft and a sleeve surrounding the longitudinal shaft;
    a sanitizing instrument constructed to house the surgical tool, the sanitizing instrument having:
        an injector head constructed to at least partially receive the surgical tool assembly, the injector head having an inlet coupling constructed to fluidly couple to a source of pressurized fluid; and
        a sanitizing body constructed to at least partially receive the tool assembly and constructed to connect to the injector head so that the tool assembly is housed between the injector head and the sanitizing body, the sanitizing body having an outlet coupling constructed to fluidly couple to a vacuum source, wherein when the tool assembly is housed in the sanitizing instrument, at least one fluid pathway is formed between the inlet coupling, the injector head, the shaft and sleeve of the tool assembly, the sanitizing body, and the outlet coupling.

14. The sanitizing system according to claim 13, further comprising:
    the source of pressurized fluid coupled to the inlet coupling, the source of pressurized fluid constructed to deliver fluid at a positive pressure to the injector head through the at least one fluid pathway; and
    the vacuum source fluidly coupled to the outlet coupling, the vacuum source constructed to apply a negative pressure to the at least one fluid pathway, wherein the simultaneous application of positive and negative pressures establish at least a predetermined pressure differential sufficient to draw the fluid through the at least one fluid pathway.

15. The sanitizing system according to claim 14, wherein the source of pressurized fluid is a syringe that is constructed to deliver at least 3 cc of fluid.

16. The sanitizing system according to claim 15, wherein the fluid includes at least one of enzymatic cleaning solution and water.

17. The sanitizing system according to claim 13, wherein the injector head and the sanitizing body extend longitudinally parallel to the tool assembly.

18. The surgical tool cleaning system according to claim 13, wherein the injector head is constructed to be threaded with respect to the sanitizing body into a seated configuration in which the injector head and the sanitizing body are sealed with each other around the tool assembly.

* * * * *